United States Patent
Igata

(10) Patent No.: US 8,330,953 B2
(45) Date of Patent: Dec. 11, 2012

(54) DETECTION METHOD AND DETECTION APPARATUS

(75) Inventor: Eishi Igata, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 338 days.

(21) Appl. No.: 12/739,358

(22) PCT Filed: Nov. 24, 2008

(86) PCT No.: PCT/JP2008/069707
§ 371 (c)(1),
(2), (4) Date: Apr. 22, 2010

(87) PCT Pub. No.: WO2009/054542
PCT Pub. Date: Apr. 30, 2009

(65) Prior Publication Data
US 2010/0240092 A1  Sep. 23, 2010

(30) Foreign Application Priority Data

Oct. 26, 2007   (JP) .................................. 2007-279553

(51) Int. Cl.
*G01N 21/00* (2006.01)
(52) U.S. Cl. ....................................... 356/337
(58) Field of Classification Search .................. None
See application file for complete search history.

(56) References Cited

U.S. PATENT DOCUMENTS

| | | | |
|---|---|---|---|
| 3,992,158 A * | 11/1976 | Przybylowicz et al. ...... | 422/428 |
| 5,184,192 A | 2/1993 | Gilby et al. | |
| 5,416,879 A | 5/1995 | Liu | |
| 7,226,862 B2 * | 6/2007 | Staehler et al. ............... | 438/689 |
| 7,402,439 B2 | 7/2008 | Kitamori et al. | |
| 2006/0046308 A1 | 3/2006 | Yamashita et al. | |
| 2009/0296083 A1* | 12/2009 | Saaski et al. .................. | 356/246 |

FOREIGN PATENT DOCUMENTS

| JP | H07-218422 A | 8/1995 |
|---|---|---|
| JP | 2002-001102 A | 1/2002 |
| JP | 3260431 B2 | 2/2002 |
| JP | 2004-113874 A | 4/2004 |
| JP | 2006-177878 A | 7/2006 |
| JP | 2006-320829 A | 11/2006 |
| JP | 2007-093374 A | 4/2007 |
| WO | 03-008981 A1 | 1/2003 |

OTHER PUBLICATIONS

Petra S. Dittrich, Kaoru Tachikawa, and Andreas Manz, "Micro Total Analysis Systems. Latest Advancements and Trends", Analytical Chemistry, 2006, vol. 78, No. 12, pp. 3887 to 3908.

Demetri Psaltis, Stephen R. Quake, and Changhuei Yang, "Developing optofluidic technology through the fusion of microfluidics and optics", Nature, 2006, vol. 442, pp. 381 to 386.

* cited by examiner

*Primary Examiner* — Tu Nguyen
(74) *Attorney, Agent, or Firm* — Canon U.S.A., Inc., IP Division

(57) ABSTRACT

Provided is a method of adjusting detection sensitivity in detecting a sample in a channel. A detection method of optically detecting a sample includes: forming a multilayer flow, in which at least one of layers of the multilayer flow contains the sample; introducing light into at least one of layers of the multilayer flow; and detecting a signal generated from the multilayer flow in response to the introduced light, to detect the sample. The sample includes one of a chemical substance, a molecule, a cell, a particle, and a mixture thereof. At least one of fluids included in the multilayer flow has a refractive index different from a refractive index of another one of the fluids.

19 Claims, 6 Drawing Sheets

DETECTION METHOD AND DETECTION APPARATUS

TECHNICAL FIELD

The present invention relates to a sample detection method and a sample detection apparatus for detecting a sample in a channel.

BACKGROUND ART

In a field of analytical chemistry, various apparatus and sensors for obtaining desired information such as concentrations or components of object to observe process or result of chemical and biochemical reactions are developed. The apparatus have been reduced in sizes with use of a semiconductor manufacturing method. In addition, a concept called "a micro total analysis system (μ-TAS)" or a "lab-on-a-chip" is under development, in which all processes for obtaining the desire information are performed on a micro device. In μ-TAS, a collected unrefined sample is caused to pass through the micro device to undergo a process such as sample refinement or chemical reaction, thereby obtaining concentration information of the component contained in the final sample or obtaining a further chemical compound. A refinement method or a chemical reaction control method used in the process, the development of a micro valve and a micro pump for use in a fluid control method, and a surface treatment method are also object to be studied in the field of the μ-TAS.

A capacity of a fluid being contained in the micro device is lower when comparing with conventional desktop-size analytical equipment. Therefore, when the micro device is used, as the reduction in the total amount of fluid is expected, the necessary amount of reagent for the use of the analysis and the length of the reaction time between the sample and the reagent are also expected to be reduced. An advantage of the micro device has been recognized and an attention has been focused on technologies associated with the μ-TAS in recent years. Phenomena such as an increase in interfacial surface to volume ratio and mixing of solutions due to diffusion, which are caused by a reduction in size of the device, have been widely studied. There have been many reports in which detection sensitivity is improved by the micro device as compared with a conventional type device (see Petra S. Dittrich, Kaoru Tachikawa, and Andreas Manz, "Micro Total Analysis Systems. Latest Advancements and Trends", Analytical Chemistry, 2006, Vol. 78, No. 12, pp. 3887 to 3908).

A device using a micro channel is constructed such that a normal channel width thereof is approximately 50 μm to 200 μm. The channel width substantially corresponds to a diameter of a multimode optical fiber. When a fluid has a higher refractive index than a material serving as the micro channel, light can be propagated through the fluid by filling the micro channel. An attention is being focused on a technology called optofluidics in which a micro fluid and light are combined together as described above. The light incident on the micro channel is repeatedly totally reflected on a channel wall surface, and then propagates through the micro fluid while the light is confined to the micro fluid on the same principle as the case where light propagates through an optical fiber (see Demetri Psaltis, Stephen R. Quake, and Changhuei Yang, "Developing optofluidic technology through the fusion of microfluidics and optics", Nature, 2006, Vol. 442, pp. 381 to 386).

A method of detecting a sample contained in a fluid filling a channel using light propagating through the fluid is disclosed, and the light is propagated through the channel made of fluorocarbon which has a lower refractive index than water, thereby detecting the sample (see Japanese Patent Application Laid-Open No. H07-218422). A method of coating an inner wall of a channel with an amorphous fluoropolymer which has a lower refractive index than water while a channel material has a higher refractive index than water, thereby confining light to the channel is also disclosed (see Japanese Patent No. 3260431).

A method using evanescent light is disclosed as a method of detecting a sample included in a channel with light at high sensitivity (see Japanese Patent Application Laid-Open No. 2006-177878). The evanescent light is generated from light propagating through an optical fiber or a waveguide. The evanescent light is light propagating while exuding to the outside of the fiber core or the waveguide, and exponentially reduces in intensity in a direction perpendicular to the propagation direction of the light. Therefore, in a case where the waveguide is formed close to the channel or to serve as an inner wall of the channel, when the evanescent light is penetrated into the channel, only a vicinity of a surface of the channel is irradiated with the light, and hence the method is suitable to detect the sample on the surface of the channel. The sample can be detected by the evanescent light at a high S/N ratio by preventing light propagating through the waveguide from being affected to the detection.

However, according to the method of detecting the sample contained in the fluid with the light propagating through the fluid using the channel made of fluorocarbon, the high-sensitivity detection is difficult because the light propagates through the entire channel, hence the S/N ratio becomes low.

Water is preferable solvent when handling a biological sample. When water is used in a channel, in order to propagate light through the channel, a device or coating material is limited to a material which has a lower refractive index than water. Examples of a material of the channel of a micro fluid device include glass, polycarbonate, cyclic polyolefin, and polydimethylsiloxane, which are frequently utilized as a micro channel material. However, each of the materials of the channel has a higher refractive index than water, and hence the detection method of propagating the light through the channel cannot be realized. Although amorphous fluoropolymer coating may be possible, some polymer material cannot be used for amorphous fluoropolymer coating. Therefore, the detection method using the amorphous fluoropolymer has a problem that there is a limit on the device material.

As to the detection method using the evanescent light generated by the waveguide located close to the channel, it is known that the detection light intensity is improved with an increase in the amount of contact between the evanescent light and the sample. In contrast to this, only the vicinity of the surface of the channel is irradiated with the evanescent light to contribute to the detection, and hence a sample which is not located close to the surface corresponds to a dead volume at the time of detection. Therefore, in order to penetrate the evanescent light into the channel and thus to detect the sample located at a position deeper than the surface of the channel, a method of adjusting one of a refractive index and a width of the waveguide can be employed. However, in the case of the conventional light detection using the waveguide, the waveguide is made of a solid material, and hence the refractive index or the width of the waveguide in the manufactured device cannot be adjusted. In other words, there is a problem that the detection sensitivity cannot be adjusted after the device is manufactured.

DISCLOSURE OF THE INVENTION

The present invention has been made in view of the above background. An object of the present invention is to provide a detection method and detection apparatus for detecting a sample contained in a fluid at high sensitivity, which are used to relax restrictions on channel materials and which have a function for adjusting detection sensitivity even after a device is fabricated.

A detection method of optically detecting a sample according to the present invention includes: forming a multilayer flow including a first fluid layer containing the sample and a second fluid layer for introducing light; introducing, into the second fluid layer, light propagating through the second fluid layer; and detecting a signal generated from the multilayer flow in response to the introduced light, to detect the sample.

A detection apparatus for optically detecting a sample according to the present invention includes: a channel for forming a multilayer flow including a first fluid layer containing the sample and a second fluid layer for introducing light; means for changing a state of the multilayer flow; means for introducing, into the second fluid layer, light propagating through the second fluid layer; and means for detecting a signal generated from the multilayer flow to detect the sample.

According to the present invention, there is an effect that a detection method and detection apparatus which are capable of adjusting at least one of a width and a refractive index of a waveguide to adjust the detection sensitivity of the sample present in a micro channel can be provided.

According to the present invention, when any one of layers of the multilayer flow in the micro channel is used as an optical waveguide, and when a position of a liquid-liquid interface is adjusted or when the optical waveguide is changed into a fluid waveguide having a different refractive index, there is another effect that the detection sensitivity of the sample can be adjusted.

According to the present invention, at least one of the multiplayer fluids is used as an optical waveguide member, and hence there is still another effect of relaxing the restriction that the channel member is required to have a refractive index lower than a refractive index of the fluid containing the sample.

According to the present invention, a detection method using evanescent light exuding from a fluidic optical waveguide to the fluid containing the sample is enabled, and hence there is still another effect that a method capable of performing high-sensitivity detection can be employed.

Further features of the present invention will become apparent from the following description of exemplary embodiments with reference to the attached drawings.

BEST MODE FOR CARRYING OUT THE INVENTION

Figure 1:
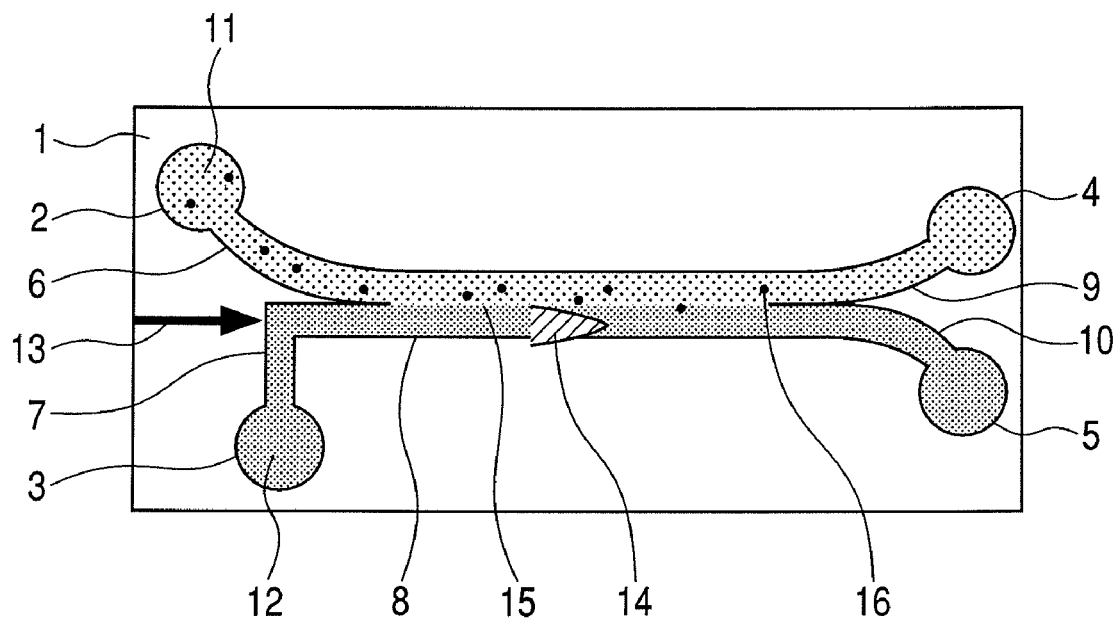
FIG. 1 is a concept view illustrating a principle of a detection apparatus according to the present invention.

Hereinafter, a detailed description of the present invention is provided.

A detection method of optically detecting a sample according to the present invention includes: forming a multilayer flow including a first fluid layer containing the sample and a second fluid layer for introducing light; introducing, into the second fluid layer, light propagating through the second fluid layer; and detecting a signal generated from the multilayer flow in response to the introduced light, to detect the sample.

The sample is preferably a chemical substance, a molecule, a cell, a particle, or a mixture thereof. The molecule may be a biomolecule such as nucleic acid or protein.

At least one of fluids included in the multilayer flow preferably has a refractive index different from a refractive index of another one of the fluids.

It is preferable that a width of the multilayer flow can be adjusted to change a cross sectional area of the second fluid layer through which the light propagates.

It is preferable that the at least one of fluids included in the multilayer flow can be changed into a fluid having a different refractive index.

The sample is preferably detected by using evanescent light existing in at least one layer of the multilayer flow.

The sample is preferably detected by scattering of light propagating through at least one layer of the multilayer flow.

The sample is preferably detected by absorption of the light propagating through the at least one layer of the multilayer flow.

The sample which can move beyond an interface between at least two layers of the multilayer flow is preferably detected.

A detection apparatus for optically detecting a sample according to the present invention includes: a channel for forming a multilayer flow including a first fluid layer containing the sample and a second fluid layer for introducing light; a mean for changing a state of the multilayer flow; a mean for introducing, into the second fluid layer, light propagating through the second fluid layer; and a mean for detecting a signal generated from the multilayer flow to detect the sample.

The mean for introducing the light is preferably a mean for introducing, into the second fluid layer, the light traveling in one of a flow direction of the second fluid layer and a direction reverse to the flow direction.

A section size of the channel is a width and height of the channel, and is preferably equal to or larger than 0.1 μm and equal to or smaller than 500 μm.

The channel for forming the multilayer flow preferably has multiple fluid injection channels into which multiple fluids are respectively injected, and the multiple fluid injection channels are met at a point located downstream of an injection point.

The mean for changing the state of the multilayer flow is preferably an apparatus capable of adjusting pressures applied to the multiple kinds of fluids. A pressure adjusting apparatus may be incorporated into a micro device. Alternatively, the pressure adjusting apparatus may be provided outside the micro device.

The mean for changing the state of the multilayer flow is preferably a mean for adjusting one of a width of at least one layer of the multilayer flow and a refractive index of at least one layer of the multilayer flow. The mean for detecting the signal is preferably one of a photo detector and a mean for collecting the signal, and is preferably provided in a position close to the channel.

The channel for forming the multilayer flow preferably has one of a portion in which one of a channel width and a channel depth is constant, a gradually narrowed portion, and/or a curved portion.

The detection apparatus preferably has a mean capable of moving the sample beyond an interface between at least two layers of the multilayer flow.

The detection apparatus preferably has a mean for stabilizing the multilayer flow in the channel for forming the multilayer flow.

According to the present invention, the multilayer flow is formed in a micro channel. Whether the flow of fluids in a certain channel is a laminar flow or a turbulent flow can be estimated based on a Reynolds number Re and is derived from the following expression:

$$Re = \frac{UL}{v} \quad [\text{Ex. 1}]$$

where U indicates a representative velocity, L indicates a representative length, and v indicates a kinematic viscosity. Although there is not a numeral value which becomes a strict boundary, when the Reynolds number is lower than approximately 2000, the fluids of the system normally form the laminar flow. In the micro channel, it is known that the Reynolds number is low. Reynolds number, in the micro channel, is normally lower than 100 and frequently becomes equal to or smaller than 1, and hence the flow of the fluids in the micro channel can be considered the laminar flow.

According to the present invention, the light is propagated through the fluids. The method uses the same fundamental as an optical fiber. The optical fiber uses a phenomenon that light is propagated through a core portion while being totally reflected because a refractive index of the core portion is set to a value higher than a refractive index of a cladding layer surrounding the core portion. The same phenomenon also holds when at least one of the core portion and the cladding layer is a fluid, and hence the behavior of light propagation can be derived from the Maxwell equation.

According to the present invention, the principle described above is used to propagate light through any part of the multilayer flow, thereby detecting the sample contained in the fluid. FIG. 1 is a concept view illustrating a detection apparatus according to an embodiment of the present invention. Hereinafter, the detection apparatus is described in detail with reference to FIG. 1.

The detection apparatus according to the present invention has a device substrate 1 and reservoirs 2 and 3 provided therein. The reservoir 2 includes a fluid 11 containing a sample 16. The reservoir 3 includes a high-refractive index fluid 12. A fluid injection channel 6 extends from the reservoir 2. A high-refractive index fluid injection channel 7 extends from the reservoir 3. The fluid injection channel 6 and the high-refractive index fluid injection channel 7 are met to form a junction 8. The fluids reaching the junction 8 move to waste reservoirs 4 and 5 through waste channels 9 and 10. At this time, the fluid 11 and the high-refractive index fluid 12 form the multilayer flow in the junction 8. Both the fluids move without being mixed in a region except for a vicinity of an interface 15, because of an environment in which the Reynolds number is low. A fluid layer including the fluid 11 containing the sample 16 is referred to as a first fluid layer. A fluid layer including the high-refractive index fluid 12 is referred to as a second fluid layer. When incident light 13 enters the high-refractive index fluid injection channel 7 to travel to the junction 8, propagation light 14 propagates in a flow direction of the multilayer flow while being confined to the high-refractive index fluid 12 serving as the second fluid layer.

That is, the second fluid layer is an optical waveguide such as a fiber, extending in the flow direction of the multilayer flow in the junction 8.

Examples of a material of the device substrate 1 include glass, ceramic, plastic, semiconductor, and a hybrid thereof. Although the material is not particularly limited, a preferable material has a minimum absorbance at a wavelength of necessary incident light. A preferable material has a chemical resistance to the sample 16, the fluid 11, and the high-refractive index fluid 12. When the device substrate 1 is to be placed in a specific environment such as a high-temperature environment, it is necessary to take a resistance thereto into account.

The respective channels 6, 7, 9, and 10 and the junction 8 have a size capable of forming the multilayer flow by the injected fluids in the junction 8, and a substantially width and depth of each thereof can be calculated based on the Reynolds number. Note that a cross sectional length corresponding to at least one of an inner width and height of the channel is preferably a channel width of approximately 100 nm to 500 μm which is normally called a micro channel width. The multilayer flow is formed corresponding to the number of injection channels, and hence the present invention is not limited to only two-layer flow as illustrated in FIG. 1. That is, a laminar flow including three layers, four layers, or five layers or a laminar flow including six or more layers may be provided. When the laminar flow including the three or more layers is provided, for example, the first fluid layer can be assumed to include the fluid containing the sample, the second fluid layer can be assumed to include the high-refractive index fluid, and a third fluid layer can be assumed as a layer for controlling a thickness of the first fluid layer.

A contact angle between the fluid injection channel 6 and the waste channel 10 and a contact angle between the high-refractive index fluid injection channel 7 and the waste channel 9 in the junction 8 can be arbitrarily set, and are preferably determined based on incident light and a detection direction.

The high-refractive index fluid 12 is preferably made of a material different in refractive index from a material of the fluid 11. The refractive index of the material of the high-refractive index fluid 12 may be adjusted by mixing the fluid 11 with another material. Alternatively, the material of the high-refractive index fluid 12 may be different in physicochemical quality from the material of the fluid 11. Note that the high-refractive index fluid 12 is preferably made of a material having a minimum absorbance at a wavelength of the incident light 13. A positional relationship between the high-refractive index fluid 12 and the fluid 11, that is, a layer structure including the first and second fluid layers is not limited to the structure illustrated in FIG. 1. In an initial state, the high-refractive index fluid 12 may be included in the reservoir 2 and the fluid 11 may be included in the reservoir 3. When the high-refractive index fluid 12 has a refractive index higher than the device substrate 1 and the fluid 11, the effect described above can be obtained.

The wavelength of the incident light 13 is preferably set to a wavelength band different from an absorbance wavelength of the device substrate 1 and an absorbance wavelength of the high-refractive index fluid 12. In addition, the wavelength of the incident light is preferably selected based on, for example, an excitation wavelength of the sample 16. More preferable incident light is coherent light such as laser light.

In FIG. 1, the sample 16 is contained in the fluid 11. The sample 16 may be further contained in the high-refractive index fluid 12 depending on a detection method. The sample 16 may be dissolved or contained without being dissolved, depending on a fluid containing the sample. Examples of the sample 16 include a chemical substance, a molecule, a cell, a particle, and a mixture thereof. The molecule includes a biomolecule such as nucleic acid or protein. However, the sample is not limited to such examples.

Each of a mean for supplying the fluid 11 and a mean for supplying the high-refractive index fluid 12 is preferably an apparatus capable of applying pressures to the fluids. For example, a syringe pump connected with a reservoir through a tube or a micro pump incorporated into the device substrate 1 may be used. Respective fluid widths in the junction 8 are determined based on the pressures applied to the fluid 11 and the high-refractive index fluid 12. The fluid widths can be arbitrarily set and obtained in advance by calculation.

A signal generated from the sample 16 is preferably detected by measuring a change in light intensity which is caused due to, for example, the fluorescence of a marker of the sample 16 or the scattering or absorption of the propagation light 14 which is produced by the sample 16. However, a detection method is not particularly limited. Examples of a detector include a CCD device for obtaining an image through an optical microscope and a photodiode for detecting a light intensity. The detector may be provided on the device substrate in a case where a semiconductor substrate is used. Therefore, it is preferable to suitably set the detector depending on a method of measuring the sample 16 which is a target. A part of the signal generated from the sample 16 may propagate through the high-refractive index fluid 12. Thus, the propagated part of the signal may be collected by, for example, an optical fiber.

The device illustrated in FIG. 1 can be manufactured at low cost by injection molding using a plastic material. An effect is further expected in which a complicated process such as a semiconductor manufacturing process is not required as compared with the conventional formation method of forming the waveguide made of the solid material.

Japanese Patent Application Laid-Open No. 2007-093374 discusses that a probe-molecule-contained liquid layer flow and an adjustment liquid layer flow are fed in parallel to a micro channel and a sample-molecule-contained liquid layer flow is fed between both the layer flows to be sandwiched therebetween, and a change in the amount of probe molecule diffused into one of the sample-molecule-contained liquid layer flow and the adjustment liquid layer flow or a change in the residual amount of probe molecule in the probe-molecule-contained liquid layer flow is detected and analyzed.

According to a discussed detection method, a light beam of 488 nm which is generated from an argon gas laser is emitted to each of a probe-molecule-contained liquid channel side and an adjustment liquid channel side which are located in predetermined positions, to cause fluorescence. Then, an intensity ratio (adjustment liquid channel side/probe-molecule-contained liquid channel side) is examined to correct analysis values affected by a variation in laser intensity and mechanical setting.

However, it is not described and suggested that the multilayer flow including the second fluid layer for introducing light is formed. It is not described and suggested that the light propagating through the fluid layer is introduced into the second fluid layer and the signal generated form the multi-layer flow in response to the introduced light is detected to detect the sample.

[Embodiments]

Hereinafter, the present invention is more specifically described with reference to embodiments. Note that the following embodiments are to describe the present invention in more detail and the present invention is not limited to only the following embodiments.

First Embodiment

Figure 2A:
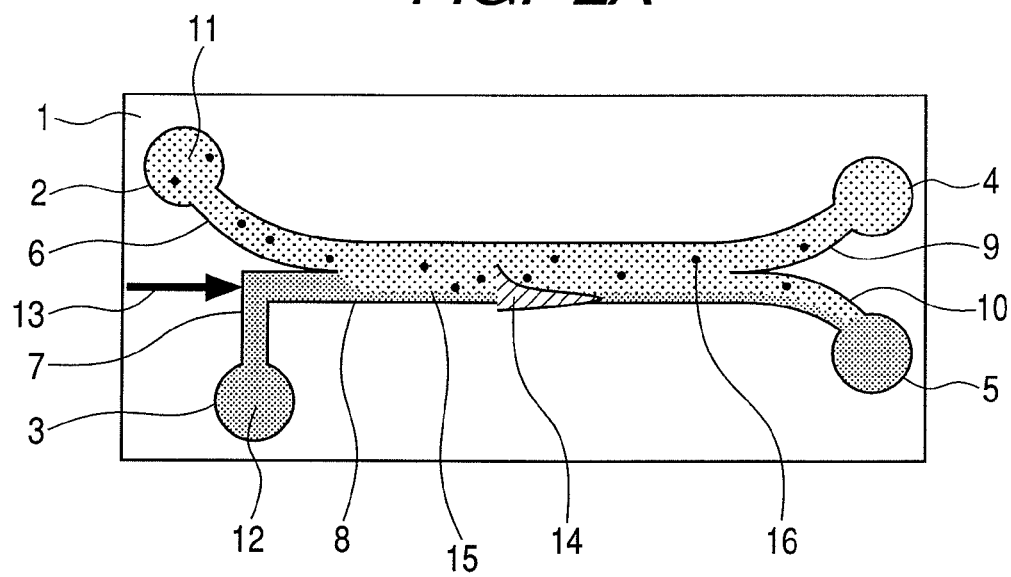
FIGS. 2A and 2B are concept views illustrating a detection apparatus according to an embodiment of the present invention.
Figure 2B:
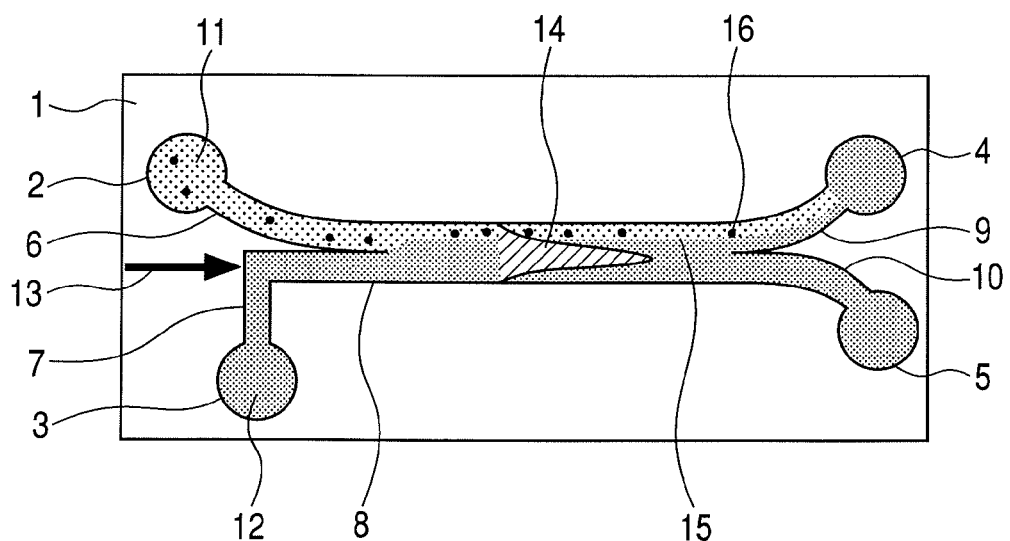

In the first Embodiment of the present invention, an application in which the fluid width is adjusted is described with reference to FIGS. 2A and 2B.

The fluid 11 included in the reservoir 2 and the high-refractive index fluid 12 included in the reservoir 3 are applied with pressures to supply the fluids to the junction 8. At this time, the fluid 11 contains the sample 16. For example, when refractive index matching oil is used as the high-refractive index fluid 12, a refractive index can be selected from a range of approximately 1.45 to 2.3. When refractive index matching oil having a small light absorbance at a use wavelength is selected, the oil is a preferable medium for the propagation light. When a main component of the fluid 11 is water, it is difficult to mix the water and the oil because of properties thereof, and hence it is expected to form a stable two-layer flow. Therefore, in the case of the fluid containing the sample whose main component is water, it is unnecessary to use a device substrate or a coating which has a refractive index lower than water.

The flows reaching the junction 8 flow to the waste reservoirs 4 and 5 while the two-layer flow is formed.

Then, the incident light 13 is emitted from the high-refractive index fluid injection channel 7 to the junction 8 to propagate through the high-refractive index fluid 12. The incident light 13 is preferably coherent light and thus corresponds to, for example, laser light. In order to reduce coupling loss between the incident light 13 and the high-refractive index fluid 12, an optical fiber may be provided close to the high-refractive index fluid injection channel 7 to make a width of the high-refractive index fluid injection channel 7 substantially equal to a width of the optical fiber.

The incident light 13 reaching the junction 8 continues to propagate through the high-refractive index fluid 12 as the propagation light 14. At this time, when the pressures applied to the fluid 11 and the high-refractive index fluid 12 are adjusted, widths of the respective fluids in the junction 8 can be adjusted. Simultaneously, the propagation light 14 propagates through the high-refractive index fluid 12 while reforms an electric field distribution corresponding to a change in width of the high-refractive index fluid 12.

The widths of the respective fluids are preferably determined based on, for example, a detection method and a purpose. For example, as illustrated in FIG. 2A, when the width of the high-refractive index fluid 12 is narrowed, an effective refractive index of the high-refractive index fluid 12 becomes lower. Therefore, the propagation light 14 reconstructs the electric field distribution to expand an evanescent region in the fluid 11. Then, a larger amount of evanescent light penetrates to the fluid 11, and hence the amount of contact to the sample 16 increases to improve detection sensitivity. A sample expected to have a high initial sample concentration is suitable as the sample 16 used in the detection method of narrowing the width of the high-refractive index fluid 12. For example, there is provided a method of detecting a nucleic acid molecule which is amplified and fluorescently-labeled, using evanescent light.

An example of the method of reducing the width or depth of the same waveguide to expand the evanescent region, thereby improving the detection sensitivity is a method employed for a surface plasmon sensor or a waveguide sensor. However, specifications of a device including the conventional solid waveguide are determined in a device design stage, and hence an error cannot be corrected in a manufacturing stage or sensitivity cannot be adjusted after manufacturing. In contrast to this, according to the present embodiment, the fluid waveguide is used, and hence a sensitivity adjustment mechanism can be provided.

The width of the high-refractive index fluid 12 can be also widened. As illustrated in FIG. 2B, when the width of the high-refractive index fluid 12 is widened, most of energy of the propagation light 14 is confined to the high-refractive index fluid 12 and only a part thereof is present as evanescent light. The sample 16 is forced to a small area of the fluid 11. Therefore, the sample 16 can be detected while a dead volume thereof is reduced. Such a detection method is used in a case where the amount of the sample 16 contained in the fluid 11 is small or in a case where it is necessary to scan a sum of the sample 16. The detection method can be applied to, for example, a cell counter. When the width of the high-refractive index fluid 12 is narrowed, the receiving sensitivity of a photodiode may exceed a saturation point because of a signal from the sample. In such a case, there is provided a method of widening the width of the high-refractive index fluid 12 to reduce a penetration distance of the evanescent light and performing the detection within a range lower than the saturation point of the photodiode.

The method of widening the width of the high-refractive index fluid 12 is also suitable to detect adsorption or chemical bonding of a substance or a sample molecule on the surface of the channel located on the fluid 11 side of the device substrate 1. For example, there is antigen-antibody reaction on the surface of the channel. An antigen contained in the fluid 11 is confined to a small region to easily react with an antibody held on the surface of the channel. Therefore, the bonding can be detected based on the evanescent light exuding from the high-refractive index fluid 12. The hybridization of DNA on the surface of the channel can be detected. However, the present invention is not limited to such examples.

As described above, according to the detection apparatus of the present invention, the detection using the evanescent light in the fluid, which is cannot be realized by the conventional fluid waveguide, can be performed. According to the detection apparatus of the present invention, the detection sensitivity of the device can be adjusted after the device is manufactured.

Second Embodiment

Figure 3:
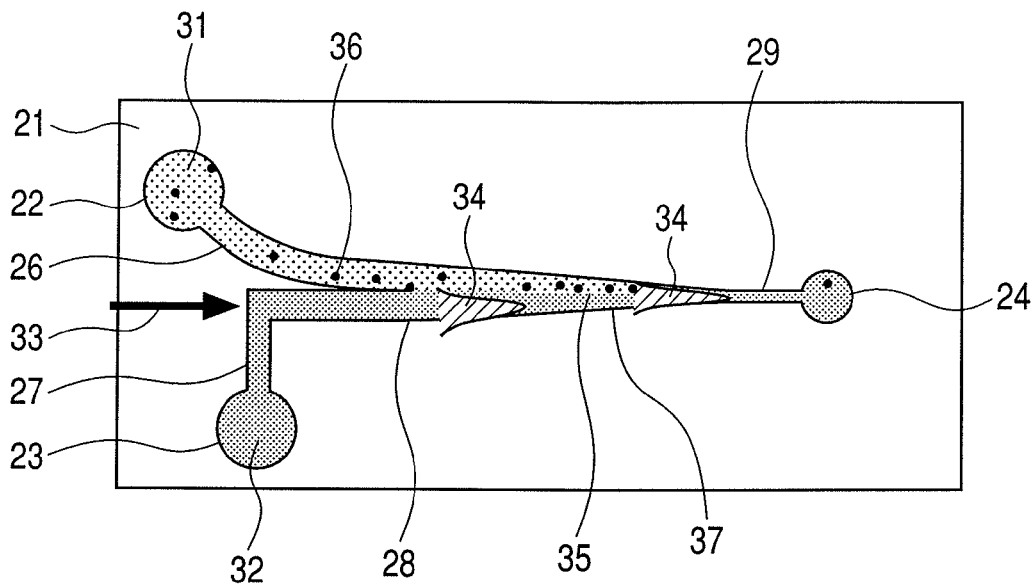
FIG. 3 is a concept view illustrating a detection apparatus using a taper portion according to an embodiment of the present invention.

In the second Embodiment of the present invention, an application in which the channel width is adjusted is described with reference to FIG. 3. Reservoirs 22 and 23 formed on a device substrate 21 include a fluid 31 and a high-refractive index fluid 32, respectively. 26, 27 and 35 indicate fluid injection channel, high-refractive index fluid injection channel and interface respectively. The respective fluids are applied with pressures to feed the fluid 31 and the high-refractive index fluid 32, thereby reaching a junction 28. The junction 28 has a taper portion 37. Both the fluids are stored in a waste reservoir 24 through a waste channel 29. A narrowing rate of the taper portion 37 can be set by calculation, and is preferably a rate of the extent to which loss of propagation light 34 is not caused by the taper portion.

After the steady two-layer flow as described above is formed, when incident light 33 is emitted to propagate through the high-refractive index fluid 32, as illustrated by the propagation light 34, the propagation light 34 propagates through the taper portion 37 while an electric field distribution thereof is reconstructed. At this time, because a width of the high-refractive index fluid 32 is narrowed, a penetration distance of evanescent light to the fluid 31 increases to improve detection sensitivity. As with the fluid 11 and the sample 16 of FIG. 2B of the first Embodiment, the fluid 31 and a sample 36 are confined to a small region. Therefore, according to the feature of this embodiment, the same state as illustrated in FIG. 2B can be constructed without precise pressure control.

Third Embodiment

Figure 4:
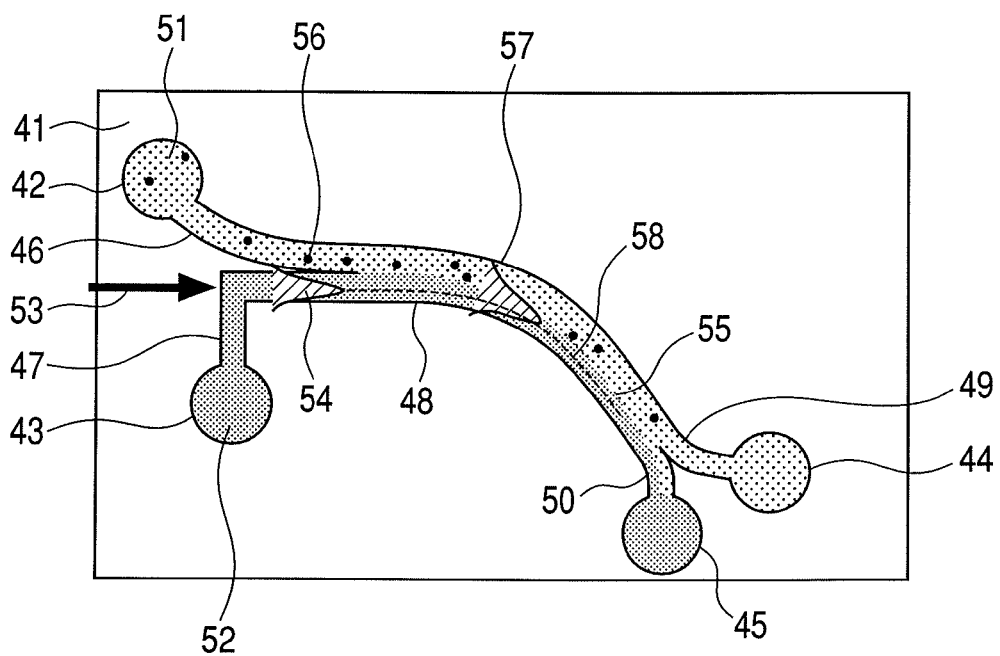
FIG. 4 is a concept view illustrating a detection apparatus using a curved portion according to an embodiment of the present invention.

In the third Embodiment of the present invention, an application in which a channel structure having a curved portion is employed is described with reference to FIG. 4.

Reservoirs 42 and 43 formed on a device substrate 41 include a fluid 51 and a high-refractive index fluid 52, respectively. The respective fluids are applied with pressures, whereby the fluid 51 and the high-refractive index fluid 52 reach a junction 48. The junction 48 has a curved portion 57 in which the high-refractive index fluid 52 is located inside. Both the fluids are stored in waste reservoirs 44 and 45 through waste channels 49 and 50. 46, 47 and 55 indicate fluid injection channel, high-refractive index fluid injection channel and interface respectively. A curvature of the curved portion 57 can be set by calculation, and is preferably a curvature of the extent to which loss of propagation light 54 is not caused by the curved portion.

Incident light 53 incident on the high-refractive index fluid 52 first propagates through a portion in which the high-refractive index fluid 52 is linear. The junction 48 has the curved portion 57, and hence the propagation light 54 is influenced by a gradient of an effective refractive index in the curved portion and propagates so as to be shifted from a center line 58 of the curved portion 57 to an outside, that is, the fluid 51 side. Therefore, evanescent light generated from the propagation light 54 is also shifted to the fluid 51 side, and hence a larger number of samples 56 are in contact with the evanescent light, thereby improving sensitivity.

The curved portion described above and the narrowed channel described in the second Embodiment can be combined to further improve the sensitivity. The taper rate and the curvature can be obtained by calculation.

Fourth Embodiment

In the fourth Embodiment of the present invention, an application in which the high-refractive index fluid is changed is described with reference to FIGS. 5A and 5B.

Reservoirs 62 and 63 formed on a device substrate 61 include a fluid 71 and a high-refractive index fluid 72, respectively. The respective fluids are applied with pressures, whereby the fluid 71 and the high-refractive index fluid 72 reach a junction 68. In the junction 68, two-layer flow is formed. Both the fluids are stored in waste reservoirs 64 and 65 through waste channels 69 and 70. 66, 67 and 75 indicate fluid injection channel, high-refractive index fluid injection channel and interface respectively.

Figure 5A:
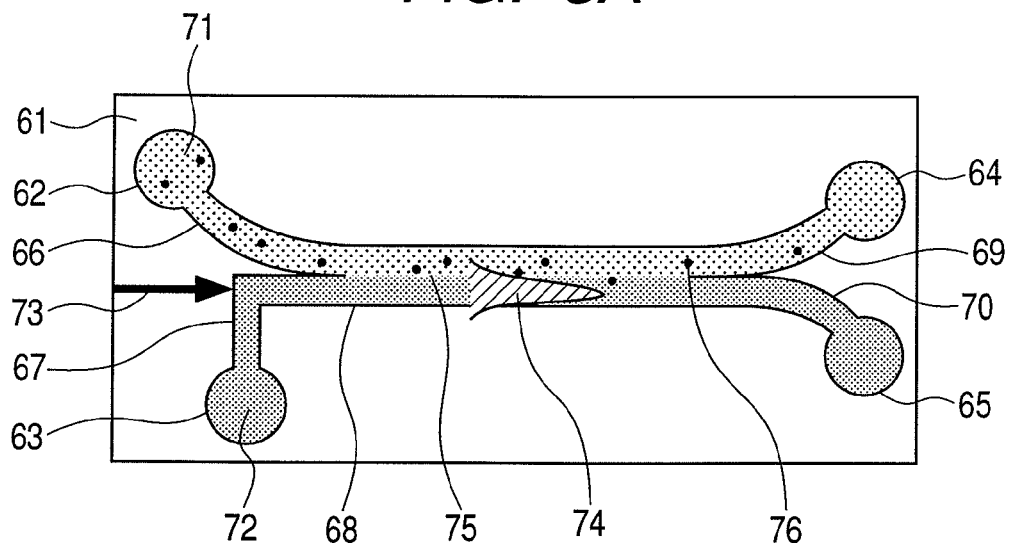
FIGS. 5A and 5B are concept views illustrating a detection apparatus in which a high-refractive index fluid is changed, according to an embodiment of the present invention.
Figure 5B:
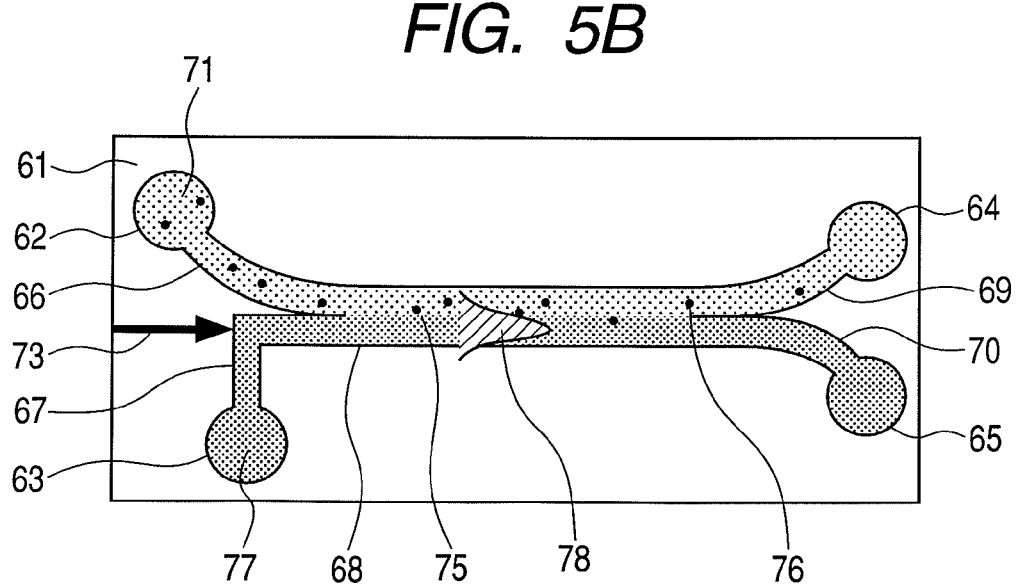

In the junction 68 illustrated in FIG. 5A, a sample 76 is detected based on evanescent light generated from propagation light 74. In this case, a penetration distance of the evanescent light to the fluid 71 side is insufficient, and hence detection sensitivity may be low. In contrast to this, as illustrated in FIG. 5B, there is provided a method of changing the high-refractive index fluid 72 of FIG. 5A into a high-refractive index fluid 77 which is different in refractive index therefrom, to adjust the sensitivity. The method is based on the fact that the penetration distance of the evanescent light increases as the refractive index of the high-refractive index fluid becomes closer to the refractive index of the fluid 71. This is because of a change in electric field distribution between the propagation light 74 of FIG. 5A and propagation light 78 of FIG. 5B. Note that the high-refractive index fluid 77 is required to have a refractive index higher than the refractive index of the device substrate 61 and the refractive index of the fluid 71.

The high-refractive index fluids 72 and 77 each are preferably made of a material having a minimum absorbance of the incident light 73.

The sensitivity adjustment method of changing the high-refractive index fluid as described in the fourth Embodiment may be combined with any one of the method of adjusting the channel width based on the pressures as described in the first Embodiment, the method of constructing the taper channel as described in the second Embodiment and the method of constructing the channel having the curved portion described in the third Embodiment. Not only a case where only two methods are combined but also, for example, a case where the high-refractive index fluid is changed in the taper channel having the curved portion may be employed. The present invention is not limited to the sensitivity adjustment methods using the channel structures as described above and the sensitivity adjustment method of changing the high-refractive index fluid. For example, a method of adjusting the wavelength of the incident light to increase the penetration distance of the evanescent light to the side of the fluid containing the sample may be employed.

As described above, the detection method using the multilayer flow includes the method of adjusting the sensitivity by various methods even after the device is fabricated. In addition, unlike the conventional detection method using the evanescent light which is generated from the propagation light in the solid waveguide and caused to penetrate to the channel, there is an effect that, even when the device does not perform a preferable operation in an initial state, it is likely to be unnecessary to refabricate the device.

Fifth Embodiment

Figure 6:
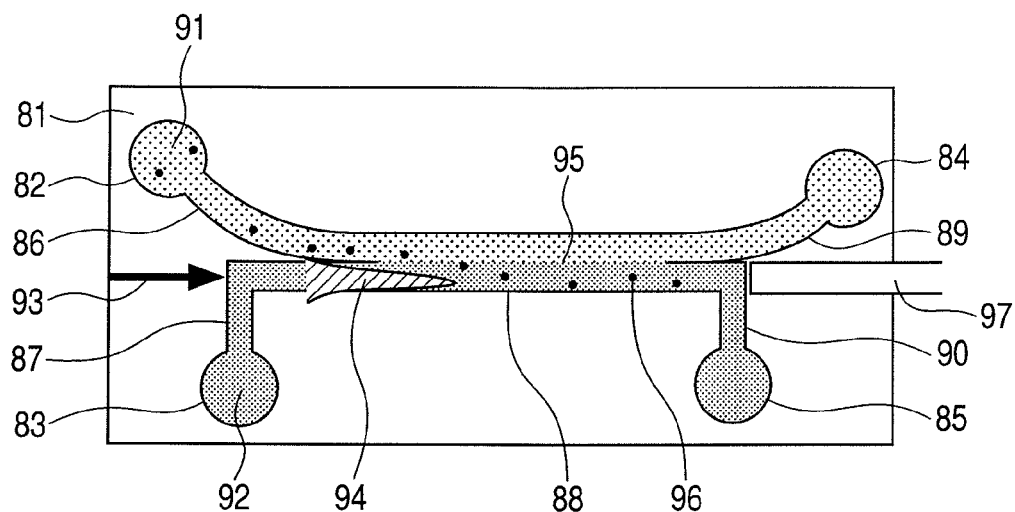
FIG. 6 is a concept view illustrating a detection apparatus using liquid-liquid extraction according to an embodiment of the present invention.

In the first to fourth Embodiments, the detection methods using the evanescent light have been described. However, the detection method according to the present invention is not limited to the detection methods using the evanescent light. An example of a detection method according to the fifth Embodiment is described with reference to FIG. 6.

Reservoirs 82 and 83 formed on a device substrate 81 include a fluid 91 and a high-refractive index fluid 92, respectively. The respective fluids are applied with pressures, whereby the fluid 91 and the high-refractive index fluid 92 reach a junction 88. In the junction 88, two-layer flow is formed. Both the fluids are stored in waste reservoirs 84 and 85 through waste channels 89 and 90. 86 and 87 indicate fluid injection channel and high-refractive index fluid injection channel respectively.

A sample 96 is included in the reservoir 82 in an initial state and fed to the junction 88 with the flow of the fluid 91. At this time, when the sample 96 has an affinity with the high-refractive index fluid 92, the sample 96 moves to the high-refractive index fluid 92 side beyond an interface 95. Incident light 93 becomes propagation light 94 propagating through the high-refractive index fluid 92. The sample 96 liquid-liquid extracted in the high-refractive index fluid 92 can be detected by scattering or absorption in the sample 96. In this case, a wavelength of each of the incident light 93 and the propagation light 94 may be set to an absorption wavelength of the sample 96. In order to more efficiently collect scattering light and absorption light, an optical fiber 97 may be provided close to the waste channel 90. A preferable diameter of the optical fiber 97 is equal to or larger than a width of the waste channel 90. An example of such a sample includes volatile hydrocarbon present in water. However, this embodiment is not limited to this.

When the liquid-liquid extraction is selectively performed, only a specific target substance such as the sample 96 contained in the fluid 91 can be entered in the high-refractive index fluid 92 side, and hence an optical detection of the specific sample can be performed. Therefore, a substance which is difficult to be labeled can also be detected.

As described in this embodiment, the fluid is used as the waveguide. Therefore, the detection apparatus according to this embodiment has an effect that the liquid-liquid extraction can be performed and the extracted substance can be measured in real time. This effect cannot be obtained in the case where the solid waveguide is used.

Sixth Embodiment

Figure 7:
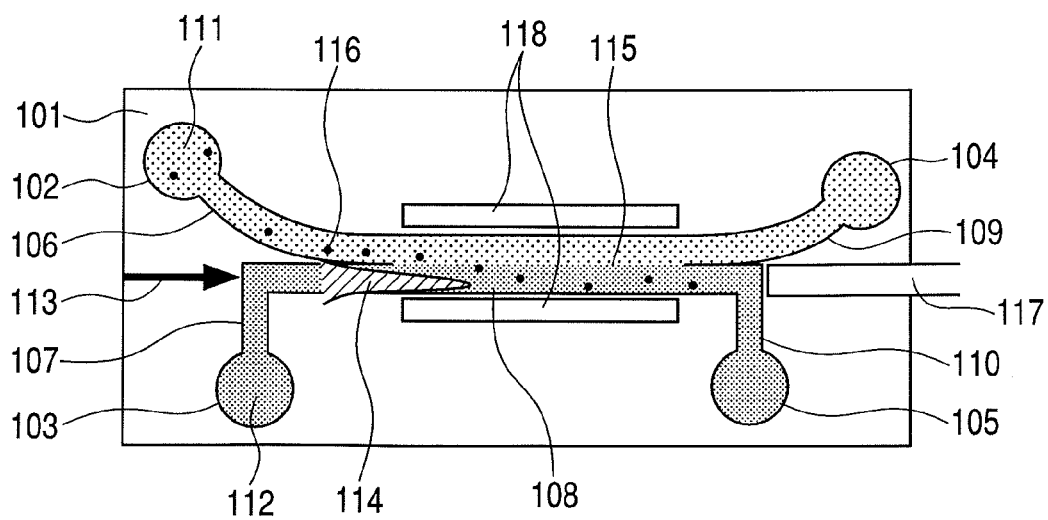
FIG. 7 is a concept view illustrating a detection apparatus using liquid-liquid extraction according to another embodiment of the present invention.

In the sixth Embodiment of the present invention, an application in which not the affinity between the sample and the high-refractive index fluid but a charged molecule or particle is measured is described with reference to FIG. 7.

Reservoirs 102 and 103 formed on a device substrate 101 include a fluid 111 and a high-refractive index fluid 112, respectively. The respective fluids are applied with pressures, whereby the fluid 111 and the high-refractive index fluid 112 reach a junction 108. In the junction 108, two-layer flow is formed. Both the fluids are stored in waste reservoirs 104 and 105 through waste channels 109 and 110. Electrodes 118 are arranged close to the junction 108, thereby providing with arbitrary polarities by the control of the outside of the device. 106, 107, 113 and 115 indicate fluid injection channel, high-refractive index fluid injection channel, incident light and interface respectively.

The electrodes 118 may serve as a side wall of the junction 108, and are preferably made of a material resistant to chemical change such as corrosion or oxidation which is caused by the fluid 111, a sample 116, or the high-refractive index fluid 112.

Assume that the sample 116 is a charged particle or molecule. The sample 116 reaching the junction 108 is separated based on the polarities of the electrodes 118. When the polarity of the sample 116 is reversed to the polarity of the electrode 118 located close to the high-refractive index fluid 112, the sample 116 enters the high-refractive index fluid 112 to be detected by propagation light 114. The example includes DNA which is specifically amplified. The DNA is normally negatively charged. Therefore, when the polarity of the electrode 118 located close to the high-refractive index fluid 112 is set to be positive, only DNA contained in an amplification reaction solution can be selectively extracted to the high-refractive index fluid 112. The amplification of the DNA sample fed to the high-refractive index fluid 112 can be determined based on an intensity of scattering light, an intensity of absorption light, or an intensity of fluorescent light in the high-refractive index fluid 112 (when DNA sample includes intercalator fluorescent pigment). A part of the fluorescent light generated from the sample 116 propagates through the high-refractive index fluid 112. Therefore, the detection may be performed after the fluorescent light is collected by an optical fiber 117 and excitation light is removed using a filter or a spectroscope, for example.

When the DNA sample including the fluorescent pigment is locally heated at an arbitrary position in the high-refractive index fluid 112 to apply, to the DNA sample, heat equal to or higher than a melting temperature of the DNA, quenching of the intercalator fluorescent pigment can be also measured. For example, infrared light is used for the local heating method. In this case, the device substrate 101 also requires a material transmitting the infrared light. However, a combination of the heating method and the device substrate 101 is not limited to this case.

Seventh Embodiment

In the seventh Embodiment, a method of forming a more stable multilayer flow, which can be applied in the present invention, is described with reference to FIGS. 8A and 8B.

In the present invention, the multilayer flow is formed. The stabilization of the multilayer flow can be improved based on a property difference between a fluid 131 and a high-refractive index fluid 132. A method of stabilizing the multilayer flow by a channel structure is described with reference to FIGS. 8A and 8B.

Figure 8A:
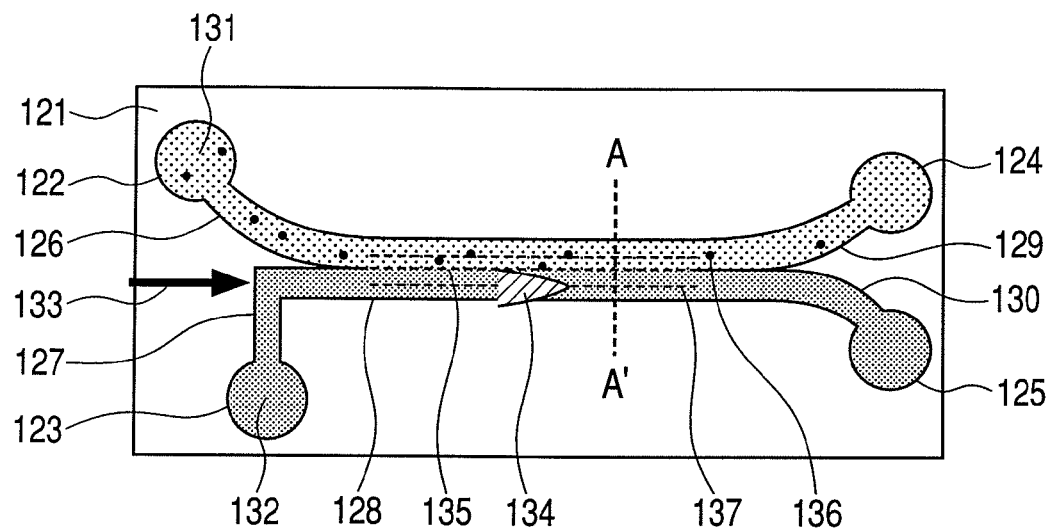
FIGS. 8A and 8B are concept views illustrating a detection apparatus using a guide according to an embodiment of the present invention.

In FIG. 8A, reservoirs 122 and 123 formed on a device substrate 121 include the fluid 131 and the high-refractive index fluid 132, respectively. The respective fluids are applied with pressures, whereby the fluid 131 and the high-refractive index fluid 132 reach a junction 128. In the junction 128, two-layer flow is formed. Both the fluids are stored in waste reservoirs 124 and 125 through waste channels 129 and 130. A guide 137 is arranged in the bottom of the channel in the junction 128. 126, 127, 133, 134 and 136 indicate fluid injection channel, high-refractive index fluid injection channel, incident light, propagation light and sample respectively.

The guide 137 is located in the bottom of the junction 128 and formed by processing the bottom of the junction 128 so as to have at least two concave portions in a direction parallel to the flow direction of the fluids. FIG. 8B illustrates an A-A' cross section of FIG. 8A. The fluid 131 and the high-refractive index fluid 132 serve as the two-layer flow in the junction 128. A channel depth of a convex portion of the guide is shallower than a channel depth of the concave portions thereof, and hence an interface tension for forming the two-layer flow can be lowered. Therefore, an interface 135 of the two-layer flow is easily stabilized by the convex portion of the guide 137. Thus, it is possible to reduce the influence of perturbation of means for applying the pressures to the fluids.

Figure 8B:
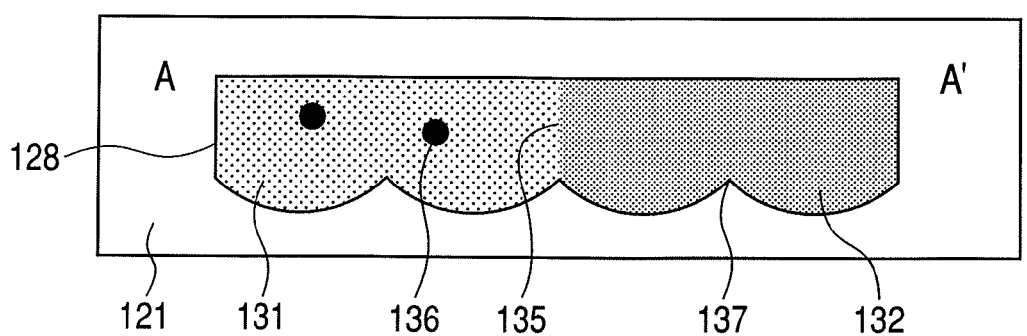

When multiple guides are provided as illustrated in FIG. 8B, the pressures applied to the fluids can be adjusted to form an interface in each guide convex portion. When the pressure applied to the fluid 131 increases, the interface 135 located in the center of the junction 128 moves to a guide convex portion located on the A'-side. When the pressure applied to the high-refractive index fluid 132 increases, the interface moves to the A-side. Therefore, when the guides are provided in arbitrary positions, the position of the interface 135 can be more stably controlled, thereby influencing the stability of detection.

In this embodiment, the multilayer flow stabilization method using the guide has been described. In order to stabilize the interface, a method of performing hydrophilic or hydrophobic treatment on the surface of the channel can also be considered. The present invention is not limited to such methods described above.

According to the present invention, light can be introduced into at least one layer of the multilayer flow to detect the sample contained in the fluid at high sensitivity. Therefore, the present invention can be used to detect, for example, a chemical substance, a molecule, or a cell in a capillary or a micro fluidic device for performing chemical synthesis, environmental analysis, and clinical sample analysis.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-279553, filed Oct. 26, 2007, which is hereby incorporated by reference herein in its entirety.

The invention claimed is:

1. A detection method of optically detecting a sample, comprising:
    forming a multilayer flow including a first fluid layer containing the sample and a second fluid layer for introducing light;
    introducing, into the second fluid layer, light propagating through the second fluid layer; and
    detecting a signal generated from the multilayer flow in response to the introduced light, to detect the sample,
    wherein the sample is detected by using evanescent light existing in at least one layer of the multilayer flow.

2. A detection method according to claim 1, wherein the introducing the light comprises introducing, into the second fluid layer, the light traveling in one of a flow direction of the second fluid layer and a direction reverse to the flow direction.

3. A detection method according to claim 1, wherein the sample comprises one of a chemical substance, a molecule, a cell, a particle, and a mixture thereof.

4. A detection method according to claim 1, wherein at least one of fluids included in the multilayer flow has a refractive index different from a refractive index of another one of the fluids.

5. A detection method according to claim 4, wherein a refractive index of a fluid included in the second fluid layer is higher than a refractive index of a fluid included in the first fluid layer.

6. A detection method according to claim 1, wherein a width of the multilayer flow is adjusted to change a cross sectional area of a layer through which the light propagates.

7. A detection method according to claim 1, wherein at least one of fluids included in the multilayer flow is changed into a fluid having a different refractive index.

8. A detection method according to claim 1, wherein the sample is detected by scattering of light propagating through at least one layer of the multilayer flow.

9. A detection method according to claim 1, wherein the sample is detected by absorption of light propagating through at least one layer of the multilayer flow.

10. A detection method according to claim 1, wherein the sample which can move beyond an interface between at least two layers of the multilayer flow is detected.

11. A detection apparatus for optically detecting a sample, comprising:
    a channel for forming a multilayer flow including a first fluid layer containing the sample and a second fluid layer for introducing light;
    means for changing a state of the multilayer flow;
    means for introducing, into the second fluid layer, light propagating through the second fluid layer; and
    means for detecting a signal generated from the multilayer flow to detect the sample,
    wherein the sample is detected by using evanescent light existing in at least one layer of the multilayer flow.

12. A detection apparatus according to claim 11, wherein the means for introducing the light comprises means for introducing, into the second fluid layer, the light traveling in one of a flow direction of the second fluid layer and a direction reverse to the flow direction.

13. A detection apparatus according to claim 11, wherein at least one of a width and a height of the channel is equal to or larger than 0.1 μm and equal to or smaller than 500 μm.

14. A detection apparatus according to claim 11, wherein:
the channel for forming the multilayer flow comprises multiple fluid injection channels into which multiple fluids are respectively injected; and
the multiple fluid injection channels are met at a point located downstream of an injection point.

15. A detection apparatus according to claim 11, wherein the means for changing the state of the multilayer flow comprises means for adjusting a width of at least one layer of the multilayer flow and/or a refractive index of at least one layer of the multilayer flow.

16. A detection apparatus according to claim 11, wherein the means for changing the state of the multilayer flow comprises means for adjusting a pressure applied to each of multiple kinds of fluids.

17. A detection apparatus according to claim 11, wherein the means for detecting the signal comprises one of a photo detector and means for collecting the signal, and is provided in a position close to the channel.

18. A detection apparatus according to claim 11, wherein the channel for forming the multilayer flow comprises one of a portion in which one of a channel width and a channel depth is constant, a portion gradually narrowed in a channel length direction, and/or a portion curved in the channel length direction.

19. A detection apparatus according to claim 11, wherein the channel for forming the multilayer flow comprises means for stabilizing the multilayer flow.

* * * * *